(12) United States Patent
Bedard et al.

(10) Patent No.: US 7,736,394 B2
(45) Date of Patent: *Jun. 15, 2010

(54) ACTUATED PROSTHESIS FOR AMPUTEES

(75) Inventors: Stephane Bedard, Quebec (CA); Pierre Olivier Roy, Sainte-Foy (CA)

(73) Assignee: Victhom Human Bionics Inc., Saint-Augustin-Desmaures, Quebec (CA)

( * ) Notice: Subject to any disclaimer, the term of this patent is extended or adjusted under 35 U.S.C. 154(b) by 307 days.

This patent is subject to a terminal disclaimer.

(21) Appl. No.: 10/721,764

(22) Filed: Nov. 25, 2003

(65) Prior Publication Data

US 2004/0181289 A1     Sep. 16, 2004

Related U.S. Application Data

(63) Continuation-in-part of application No. 10/463,495, filed on Jun. 17, 2003, now Pat. No. 7,314,490.

(60) Provisional application No. 60/405,281, filed on Aug. 22, 2002, provisional application No. 60/424,261, filed on Nov. 6, 2002, provisional application No. 60/453,556, filed on Mar. 11, 2003.

(51) Int. Cl.
   *A61F 2/64* (2006.01)
   *A61F 2/70* (2006.01)

(52) U.S. Cl. ........................................ 623/24; 623/44

(58) Field of Classification Search .............. 623/24, 623/39, 44
See application file for complete search history.

(56) References Cited

U.S. PATENT DOCUMENTS

| | | | |
|---|---|---|---|
| 4,030,141 A | 6/1977 | Graupe | |
| 4,179,759 A | 12/1979 | Smith | |
| 4,521,924 A | 6/1985 | Jacobsen et al. | |
| 4,558,704 A | 12/1985 | Petrofsky | |
| 4,994,086 A | 2/1991 | Edwards | |
| 5,062,856 A | 11/1991 | Sawamura et al. | |
| 5,062,857 A | 11/1991 | Berringer et al. | |
| 5,133,773 A | 7/1992 | Sawamura et al. | |
| 5,133,774 A | 7/1992 | Sawamura et al. | |
| 5,252,102 A | 10/1993 | Singer et al. | |

(Continued)

FOREIGN PATENT DOCUMENTS

DE         42 29 330 A1      3/1994

(Continued)

OTHER PUBLICATIONS

English translation of EP 1 169 982 A1.*

(Continued)

*Primary Examiner*—David H. Willse
(74) *Attorney, Agent, or Firm*—Polsinelli Shughart PC; Timothy J. Keefer

(57) ABSTRACT

The actuated leg prosthesis comprises a knee member, a socket connector provided over the knee member, an elongated trans-tibial member having a bottom end under which is connected an artificial foot, and a linear actuator. A first pivot assembly allows to operatively connect the trans-tibial member to the knee member. A second pivot assembly allows to operatively connect an upper end of the actuator to the knee member. A third pivot assembly allows to operatively connect a bottom end of the actuator to the bottom end of the trans-tibial member. The prosthesis can be provided as either a front actuator configuration or a rear actuator configuration.

22 Claims, 17 Drawing Sheets

U.S. PATENT DOCUMENTS

| | | | |
|---|---|---|---|
| 5,383,939 A | 1/1995 | James | |
| 5,443,528 A | 8/1995 | Allen | |
| 5,571,205 A | 11/1996 | James | |
| 5,571,213 A | 11/1996 | Allen | |
| 5,650,704 A | 7/1997 | Pratt et al. | |
| 5,704,946 A | 1/1998 | Greene | |
| 5,746,774 A | 5/1998 | Kramer et al. | |
| 5,779,735 A | 7/1998 | Molino | |
| 5,888,212 A | 3/1999 | Petrofsky et al. | |
| 5,888,213 A | 3/1999 | Sears et al. | |
| 5,888,246 A | 3/1999 | Gow | |
| 5,893,891 A | 4/1999 | Zahedi | |
| 5,895,430 A | 4/1999 | O'Connor | |
| 6,007,582 A | 12/1999 | May | |
| 6,113,642 A | 9/2000 | Petrofsky et al. | |
| 6,206,932 B1 * | 3/2001 | Johnson | 623/38 |
| 6,361,570 B1 | 3/2002 | Gow | |
| 6,425,925 B1 | 7/2002 | Grundei | |
| 6,494,039 B2 | 12/2002 | Pratt et al. | |
| 2001/0029400 A1 | 10/2001 | Deffenbaugh et al. | |
| 2002/0052663 A1 | 5/2002 | Herr et al. | |
| 2002/0198604 A1 | 12/2002 | Schulman et al. | |
| 2004/0064195 A1 | 4/2004 | Herr | |
| 2004/0193286 A1 | 9/2004 | Grundei | |
| 2006/0249315 A1 | 11/2006 | Herr et al. | |
| 2007/0016329 A1 | 1/2007 | Herr et al. | |
| 2007/0043449 A1 | 2/2007 | Herr et al. | |
| 2007/0123997 A1 | 5/2007 | Herr et al. | |
| 2007/0162152 A1 | 7/2007 | Herr et al. | |

FOREIGN PATENT DOCUMENTS

| | | |
|---|---|---|
| EP | 0 549 855 A2 | 7/1993 |
| EP | 1 166 726 A1 | 1/2002 |
| EP | 1 169 982 A1 | 1/2002 |
| FR | 2 623 086 | 5/1989 |
| FR | 2623086 | 5/1989 |
| GB | 2 201 260 | 8/1988 |
| GB | 2 260 495 | 4/1993 |
| GB | 2 302 949 A | 2/1997 |
| JP | 11056885 | 3/1999 |
| JP | 2001277175 | 10/2001 |
| JP | 2002-191654 A * | 7/2002 |
| WO | WO 96/41599 | 12/1996 |
| WO | WO 99/08621 | 2/1999 |
| WO | WO 00/38599 | 7/2000 |
| WO | WO 01/72245 | 10/2001 |

OTHER PUBLICATIONS

Flowers et al., Journal of Biomechanical Engineering: Transactions of the ASME: Feb. 1977, pp. 3-8.*

English translation of Ota, JP 2002-191654 A.*

EPO—International Search Report, Dec. 5, 2003 : PCT/CA03/00902.

English Translation of JP 2002-191654 A.

Dietl, H., Der Einsatz von Elektronik bei Prothesen zur Versorgung der unteren Extremitat, Med. Orth. Tech. 117 (1997) 31-35.

Flowers et al., Journal of Biomedical Engineering: Transactions of the ASME; Feb. 1977, pp. 3-8.

* cited by examiner

ACTUATED PROSTHESIS FOR AMPUTEES

CROSS-REFERENCE TO RELATED APPLICATIONS

The present application is a Continuation-in-Part of U.S. application 10/463,495 filed Jun. 17, 2003, now U.S. Pat. No. 7,314,490, and claims the benefits of U.S. provisional patent applications No. 60/405,281 filed Aug. 22, 2002; No. 60/424,261 filed Nov. 6, 2002; and No. 60/453,556 filed Mar. 11, 2003, all of which are hereby incorporated by reference.

TECHNICAL FIELD

The present invention relates to an actuated prosthesis for amputees, particularly but not exclusively for a leg prosthesis for above knee amputees.

BACKGROUND

Over the years, many kinds of prostheses have been devised in effort to replace the limbs that amputees have lost. In particular, many efforts have been made to develop prostheses that will replace the loss of major limbs such as legs and arms in view of the immense impact that such a loss has on the amputee. All these prostheses have the difficult task of giving to these amputees a life as normal as possible. The task is particularly difficult for leg prostheses due in part to the complexity of human locomotion. Conventional leg prostheses have until now only been using passive mechanisms in the most sophisticated available devices. Conventional leg prostheses are very limited compared to a real human leg and some needs were thus not entirely fulfilled by them.

According to amputees, specific conditions of use of conventional leg prostheses, such as repetitive movements and continuous loading, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

Another problem is that during the amputees' locomotion, energy used for moving the prosthesis mainly originates from the amputees themselves because conventional leg prostheses do not have self-propulsion capabilities. This has considerable short and long-term negative side effects. Recent developments in the field of energy-saving prosthetic components have partially contributed to improve energy transfer between the amputees and their prosthesis. Nevertheless, the problem of energy expenditure is still not fully resolved and remains a major concern.

A further problem is that the dynamic role played by the stump during the amputees' locomotion renders difficult the prolonged wearing of conventional leg prostheses. This may create, among other things, skin problems such as folliculitis, contact dermatitis, oedema, cysts, skin shearing, scarring and ulcers. Although these skin problems may be partially alleviated by using a silicone sheath, a complete suction socket or powder, minimizing these skin problems remain a concern.

Similar considerations apply in other prostheses, to a greater or lesser extent as dictated by the particular conditions that are imposed on the prosthesis.

It is therefore an object of the present invention to obviate or mitigate the above disadvantages.

SUMMARY

In accordance with a first broad aspect of the present invention, there is provided an actuated prosthesis for replacement of an amputated limb, the prosthesis comprising:
  a primary joint member; a socket connector assembly for connecting a socket to said primary joint member;
  an elongated structural member having opposite ends spaced apart along, a main longitudinal axis;
  a connector assembly for connecting a terminal portion to an end of said structural member;
  a pivot assembly for operatively connecting the structural member to the primary joint member to permit relative rotation between said primary joint member and said structural member about an first axis defined by said pivot assembly;
  a linear actuator connected at one end to said structural member and at the opposite end to said primary joint member at a location spaced from said pivot assembly, whereby extension or retraction of said actuator induces a corresponding rotation of said primary joint member relative to said structural member about said pivotal axis.

Preferably, said prosthesis is a leg prosthesis and said actuator is electrically powered.

In accordance with another broad aspect of the present invention, there is provided an improved actuated leg prosthesis comprising a knee member, a socket connected to the knee member, an elongated trans-tibial member, an artificial foot connected under a bottom end of the trans-tibial member, and a linear actuator. A first pivot assembly allows to operatively connect the trans-tibial member to the knee member. The first pivot assembly defines a first pivot axis that is perpendicular to a main longitudinal axis of the trans-tibial member. A second pivot assembly allows to operatively connect an upper end of the actuator to the knee member. The second pivot assembly defines a second pivot axis that is substantially parallel to the first pivot axis. The second pivot axis is also spaced apart from the first pivot axis and the main longitudinal axis. A third pivot assembly allows to operatively connect a bottom end of the actuator to the bottom end of the trans-tibial member. The third pivot assembly defines a third pivot axis that is substantially parallel to and spaced apart from the first pivot axis.

Embodiments of the present invention will now be described by way of example only with reference to the accompanying drawings in which.

DETAILED DESCRIPTION

The appended figures show three alternative embodiments of an actuated prosthesis (10) implemented as a leg prosthesis for an above knee amputee. It should be understood that the present invention is not limited to these illustrated implementations since various changes and modifications may be effected herein without departing from the scope of the appended claims and the principles and concepts described may be applied to prosthesis to replicate other limbs such as an arm. For clarity and ease of description, terminology relating to the use as a leg has been utilized but it will be understood that terminology applicable to the equivalent functions in other limbs may be used. For example, reference to a "knee" could be described equally with respect to an "elbow" if the prosthesis is an arm.

As illustrated, the prosthesis (10) has three alternative configurations, one being a front actuator configuration, another being a rear actuator configuration and the other being an inverted actuator configuration. The front actuator configuration is preferred. FIGS. 1 to 7 show the prosthesis (10) with the front actuator configuration while FIGS. 8 to 13 show the prosthesis (10) with the rear actuator configuration.

FIGS. 15 to 21 show the inverted actuator configuration.

Front Actuator Configuration

Figure 1:
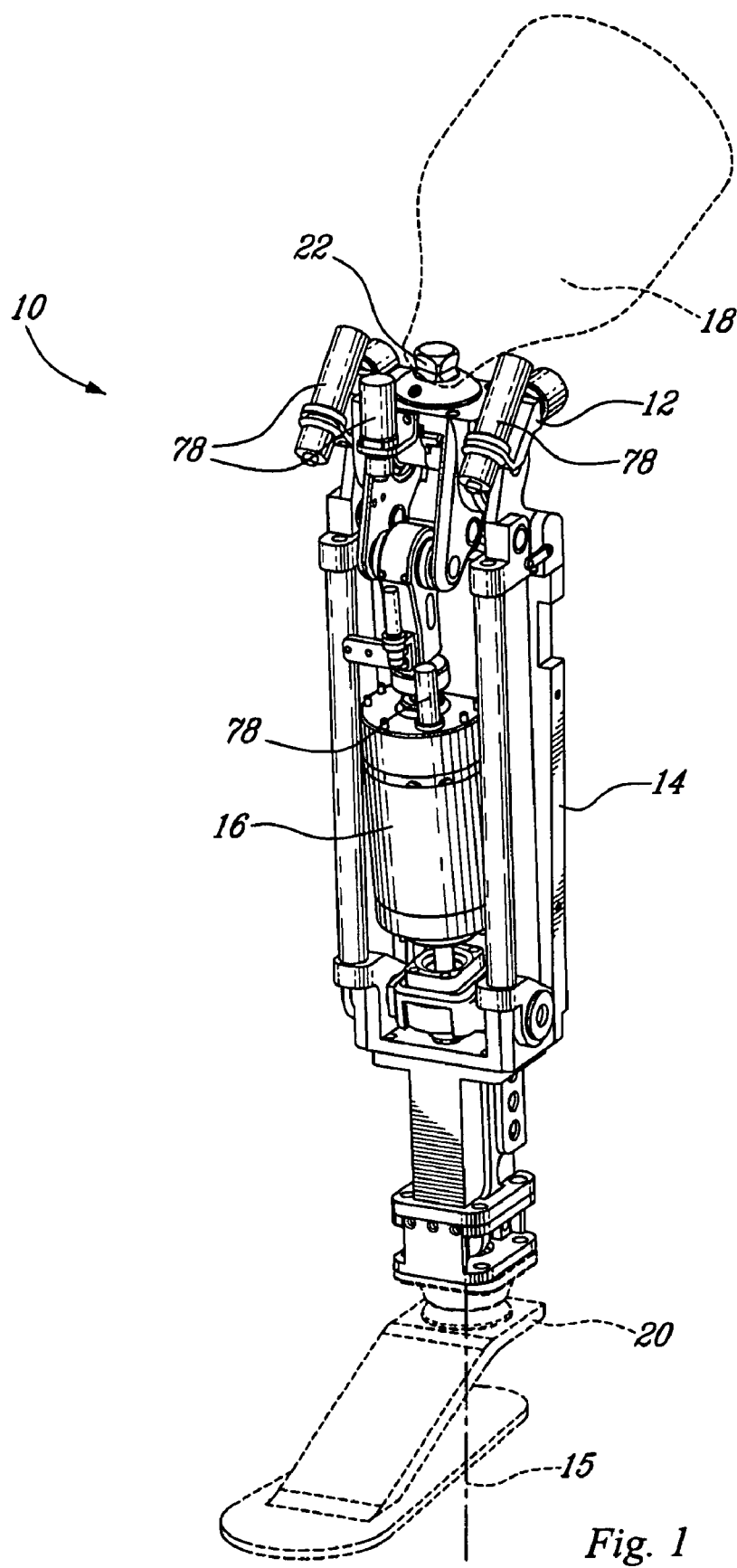
FIG. 1 is a perspective view of an actuated prosthesis with a front actuator configuration.
Figure 2:
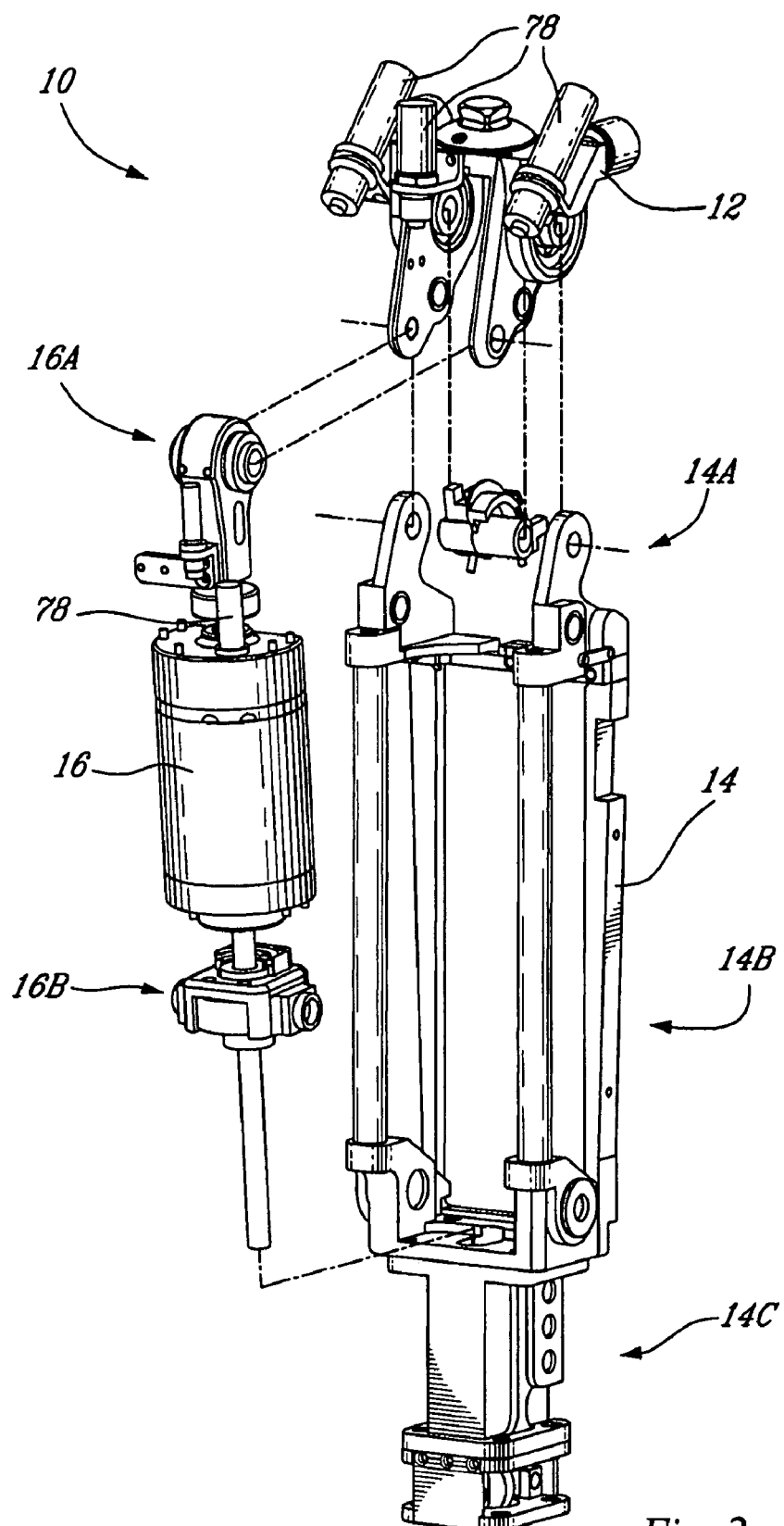
FIG. 2 is a partially exploded perspective view of the prosthesis shown in FIG. 1.

FIGS. 1 and 2 show the basic components of the prosthesis (10), which include a primary joint referred to as a knee member (12), an elongate structural member referred to as an elongated trans-tibial member (14), and a linear actuator (16) acting between the knee member (12) and the trans-tibial member (14) to cause relative movement between them. The prosthesis (10) also comprises a socket connector assembly (17) for connecting a socket (18) on the knee member (12) and a connector assembly (19) for connecting to a terminal portion of a limb such as an artificial foot (20) under a bottom end of the trans-tibial member (14).

The socket (18) must achieve adequate effort transfers between the prosthesis (10) and the amputee's stump. The design of the socket (18) is usually a custom operation in order to achieve an optional load transmission, stability and efficient control for the stump's mobility. The socket (18) is generally held in place on the stump of the user by a suction effect created by an appropriate system such as, for example, a flexible suction liner of type "Thermolyn" manufactured by the Otto Bock Inc. The prosthesis (10) can otherwise use any suitable sockets available on the market.

The socket assembly connector (17) for connecting the socket (18) may comprise a bottom socket connector (22) provided over the knee member (12). The bottom socket connector (22) is preferably removably connected by means of fasteners, for instance screws or bolts. The exact type of bottom socket connector (22) may vary. An example is a connector having a standard male pyramid configuration, such as male pyramid model 4R54 manufactured by Otto Bock Inc. Another example is the sliding connector with male pyramid model 2054-2 manufactured by Ossur Inc. The socket (18) would then be equipped with a corresponding upper connector which fits over the bottom male connector (22). Other types of connectors may be used as well.

The knee member (12) provides the junction between the socket (18) and the trans-tibial member (14) with at least one degree of freedom in rotation. The knee member (12) range of motion is preferably about 105 degrees, where zero degree is at full extension and 105 degrees is at maximal knee flexion.

Figure 3:
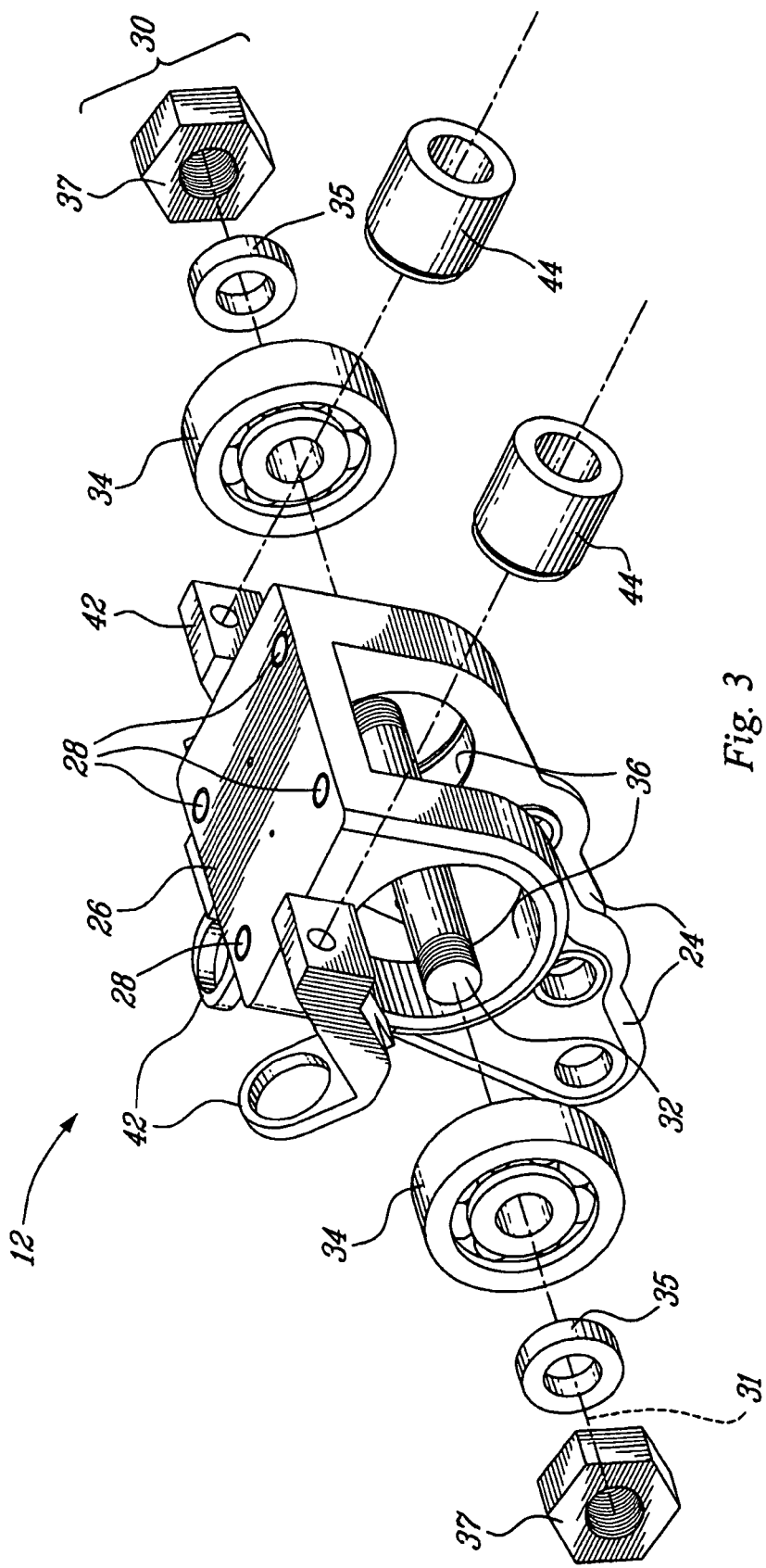
FIG. 3 is an exploded perspective view of the knee member and the first pivot assembly shown in FIG. 1.

FIG. 3 shows an enlarged view of the knee member (12). The knee member (12) is preferably a fork-shaped item, with two flanges (24) projecting from an upper plate (26). The upper plate (26) includes four threaded holes (28) for the removable fasteners of the bottom socket connector (22).

The knee member (12) is connected to the trans-tibial member (14) by means of a first pivot assembly (30). The first pivot assembly (30) operatively connects the trans-tibial member (14) to the knee member (12), thereby making possible a relative rotation between these two parts. It should be noted that the first pivot assembly (30) can also be polycentric. This means that the movement between the knee member (12) and the trans-tibial member (14) is not purely rotational but follows a much more complex pattern. The right and left sides of the parts can further be slightly different, thereby causing a slight torsion movement around a vertical axis. Nevertheless, the general overall movement remains substantially a rotation around a pivot axis.

Figure 4:
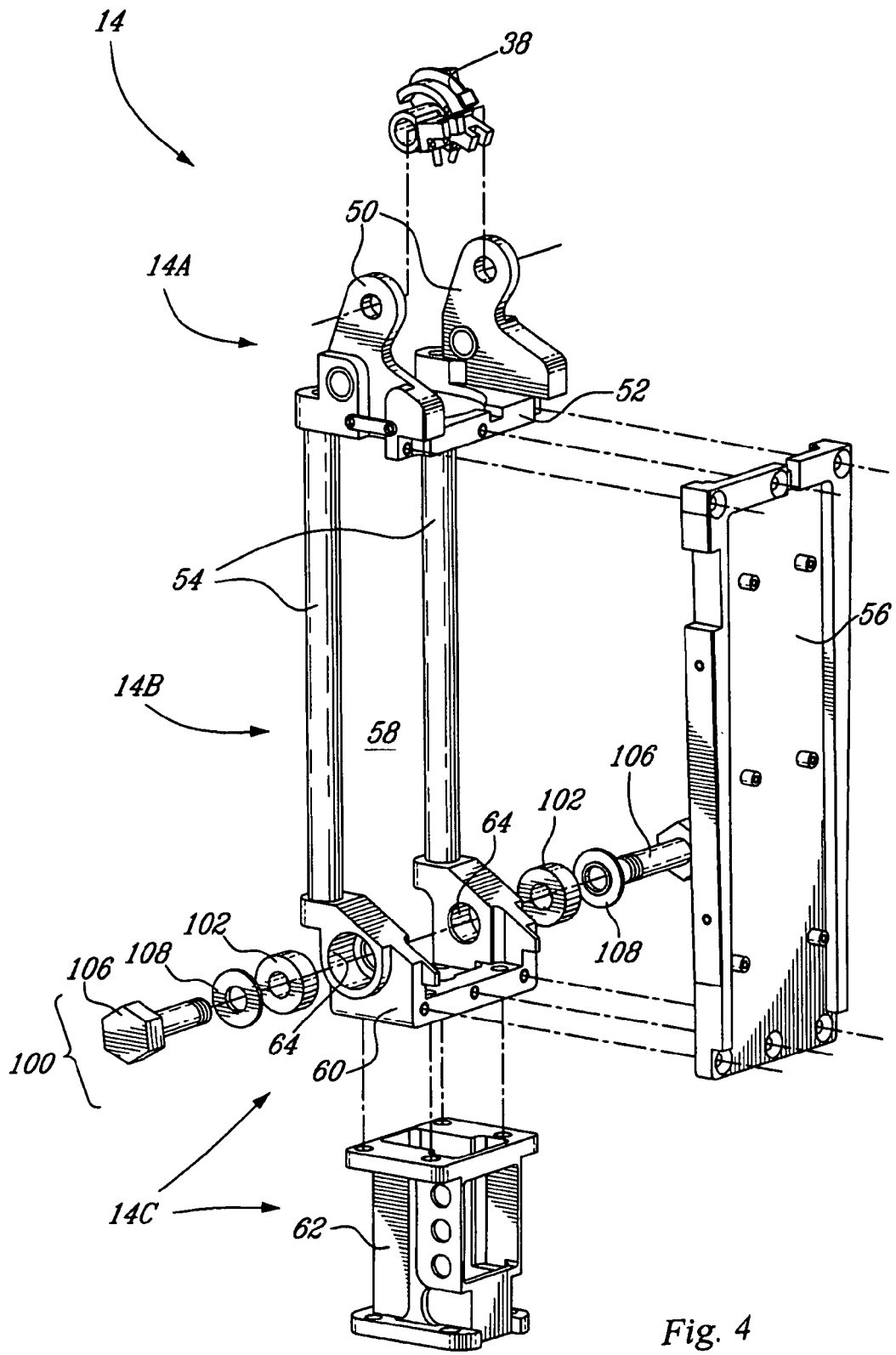
FIG. 4 is an exploded view of the trans-tibial member and the third pivot assembly shown in FIG. 1.
Figure 7:
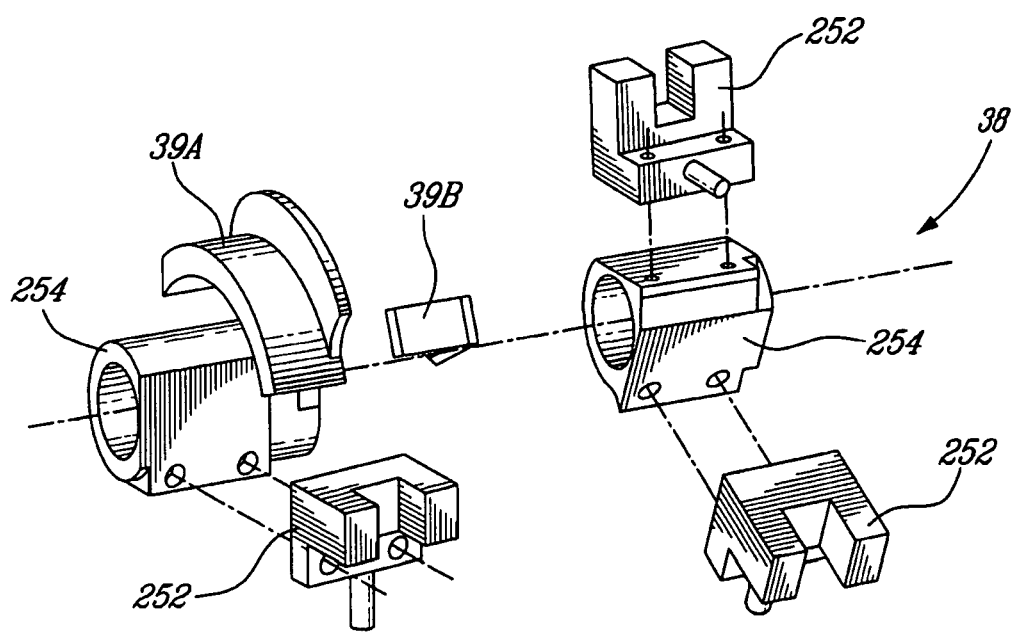
FIG. 7 is an exploded view of the optical switch support shown in FIG. 4.

The first pivot assembly (30) defines a first pivot axis (31) that is substantially perpendicular to a main longitudinal axis (15) extending along the length of trans-tibial member (14) in the frontal plane, as shown in FIG. 1. This first pivot assembly (30) comprises an axle (32) supported by two bearings (34), each mounted in a corresponding housing (36) in the flanges (24) of the knee member (12). An example of bearing (34) is a single groove-bearing model 6300-ZZ manufactured by NSK Inc. Of course, other types of bearings (34) may be used as well. A 10 mm shoulder nut (37) and a set of external spacers (35) retain the bearings (34) on threaded ends of the axle (32). An optical switch support (38), shown in FIGS. 2, 4 and 7, is mounted around the axle (32) between the two flanges (24) of the knee member (12). The support (38) is described later in the description.

Preferably, as best shown in FIG. 3, a set of energy absorption bumpers (44) is provided at the back side of the knee member (12) to prevent out of range motion.

These bumpers (44) can be, for example, bumper model GBA-1 manufactured by Tecspak Inc. Of course, other types of bumpers (44) may be used as well. They are mounted on corresponding brackets (42) located on the side and the front of the upper plate (26) of the knee member (12). The brackets

(42) are also used to support connectors (78) which are described later in the description.

As can best be seen in FIG. 4, the trans-tibial member (14) includes three main sections, namely an upper section (14A), a middle section (14B), and a bottom section (14C).

The upper section (14A) of the trans-tibial member (14) is preferably a fork-shaped item with two flanges (50) projecting from a mounting base (52). The mounting base (52) is rigidly connected to a pair of trans-tibial post bars (54). A back plate (56) is provided at the back. The pair of bars (54) and the back plate (56) are part of the middle section (14B). They are both connected to the bottom section (14C), which is itself formed from two parts (60, 62). The first part (60) is a somewhat U-shaped part under which the second part (62) is attached. The second part (62) is an extension under which the artificial foot (20) is provided. The foot connector assembly (19) for connecting the artificial foot (20) includes a set of threaded holes in which screws are inserted. Other types of connectors may be used.

The artificial foot (20) may be, for example, a standard 26cm Trustep prosthetic foot manufactured by College Park Industries Inc. or Allurion model ALX5260 prosthetic foot manufactured by Ossur Inc. Other types of articulated or non-articulated artificial foot (20) may be used if the selected prosthetic foot provides approximately at least the same dynamical response as the ones mentioned here above. The design of the prosthesis (10) is modular and consequently, it can be adjusted to any morphology. The artificial foot (20) may have an exposed metal or composite structure. It may also have a cosmetic covering that gives it the appearance of a human ankle and foot.

The pair of bars (54) and the back plate (56) provide a space (58) in which most of the actuator (16) is located. The various electronic and electric components may also be attached on either sides of the back plate (56). This compact arrangement keeps the overall dimensions within that of a normal human leg.

Figure 5:
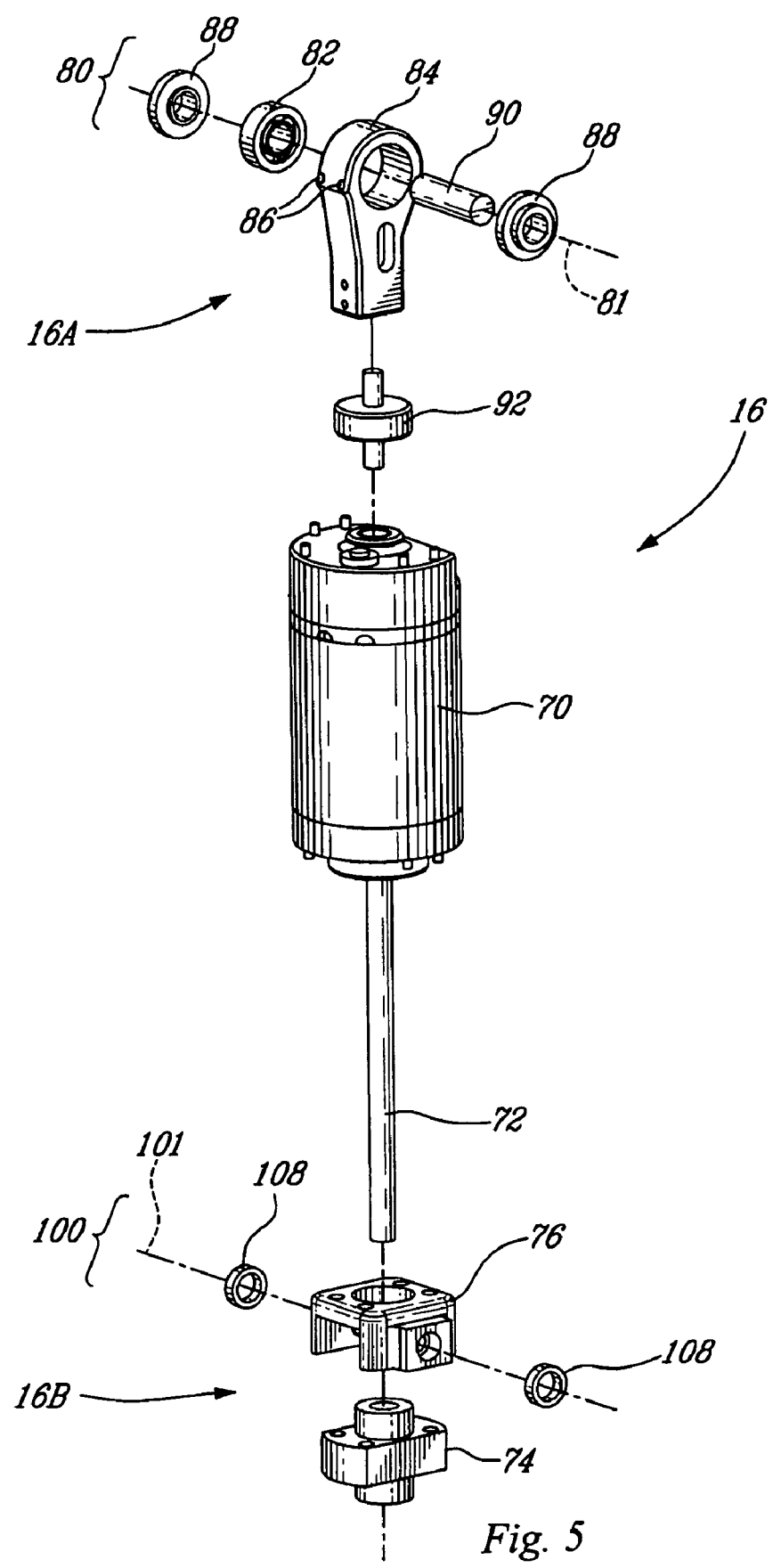
FIG. 5 is a partially exploded view of the linear actuator and the second pivot assembly shown in FIG. 1.

The linear actuator (16) is shown in FIG. 5. The upper end (16A) of the actuator (16) is connected to the knee member (12) by a pivot assembly 80and the bottom end (16B) is connected to the bottom section (14C) of the trans-tibial member (14). The function of the actuator (16) is to supply the prosthesis (10) with the necessary mechanical energy to execute, in a sagittal plane, the angular displacements synchronized with the amputee's locomotion. The linear motion of the actuator (16) is used to control the angle of the knee member (12) with reference to the trans-tibial member (14). The actuator (16) includes an electrical motor (70) coupled with a mechanism (72, 74) to transfer rotational motion into linear motion. An example of motor (70) is the model BN2328EU manufactured by Poly-Scientific. The motor (70) operates a screw (72) engaged to a fixed follower (74) at the bottom of the actuator (16). The follower (74) is held by a follower support (76). The follower (74) and the follower support (76) constitute the bottom end (16B) of the actuator (16). In use, when the motor (70) rotates, the screw (72) is rotated in or out of the follower (74). This pushes or pulls the knee member (12), thereby causing a relative rotation between the knee member (12) and the trans-tibial member (14).

The choice of the linear actuator (16) is primarily based on weight versus torque ratio and speed of available motor technologies. It is preferred over a direct drive system coupled directly to the knee member (12) because it takes less space for the torque requirement in human locomotion. It was found that ideally, the actuator (16) must be capable of supplying a continuous force of about 515 N and a peak force of about 2250 N.

Figure 6:
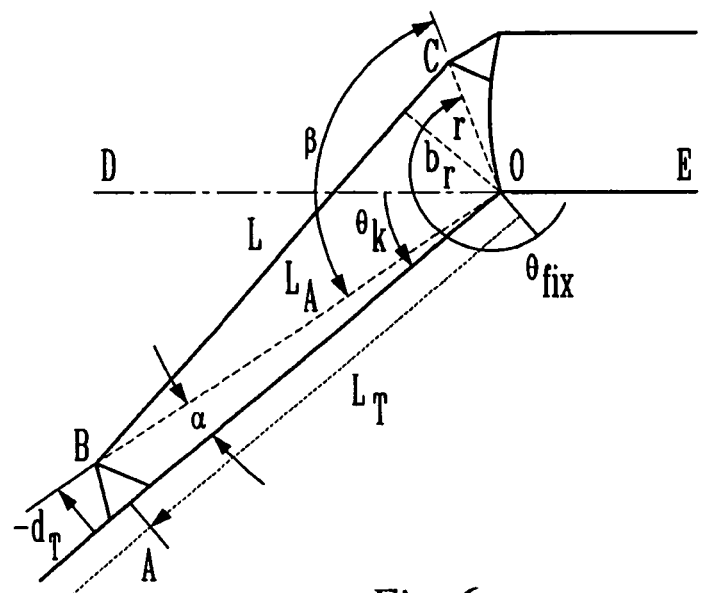
FIG. 6 is a diagram illustrating the geometrical model with the front actuator configuration.

The second pivot assembly (80) operatively connects the upper end (16A) of the actuator (16) to the knee member (12). The second pivot assembly (80) defines a second pivot axis (81) that is substantially parallel to the first pivot axis (31). It is also spaced from the plane defined by its first pivot axis (31) and the main longitudinal axis (15). An example of this configuration is schematically illustrated in FIG. 6. This diagram represents the various pivot axes. The first pivot axis (31) is identified as "O". The second pivot axis (81) is identified with the letter "C". Both axes (C, 0) are spaced apart by the distance "r". This distance creates a lever arm allowing the actuator (16) to move the trans-tibial member (14) with reference to the knee member (12).

FIG. 5 shows that the second pivot assembly (80) comprises a bearing (82) inserted in a mechanical connector (84) forming the upper end (16A) of the actuator (16). The bearing (82) may be a needle bearing, for example needle bearing model NK14/16 manufactured by INA Inc. It is held in place by means of shoulder screws (86) and aluminum spacers (88). It was found that ideally, the bearing (82) must withstand a static charge up to about 11500 N (2600 lbf) and allows for a typical misalignment of 1 to 3. The needle bearing (82) is preferred since it has practically no mechanical play and a low coefficient of friction when compared to bushing or rod ends. Of course, other types of bearings may be used as well. An axle (90) links the mechanical connector (84) to corresponding holes in the flanges (24) of the knee member (12). The mechanical connector (84) is secured over the motor (70) using a load cell (92), which is described later in the description.

The bottom end (16B) of the actuator (16) is operatively connected to the trans-tibial member (14) using a third pivot assembly (100), as shown in FIGS. 4 and 5. The third pivot assembly (100) defines a third pivot axis (101) and also preferably comprises one or more needle bearings (102), each mounted in a corresponding housing (64) provided in the first part (60) of the bottom section (14C) of the trans-tibial member (14). Two standard needle bearings (102) may be used for that purpose, for example needle bearing model NK14/16 manufactured by INA Inc. Of course, other types of bearings may be used as well in the second (80) and the third pivot assembly (100). A set of screws (106) and spacers (108) completes the third pivot assembly (100).

The various structural parts of the prosthesis (10) are preferably made of a light material, for instance aluminum or a composite material, such as carbon fiber, fiberglass or the like. A particularly suitable material is thermally treated 6061T6 aluminum. The various parts are preferably screwed together, although they may be welded and otherwise secured together Screwing the parts together is preferred since this increases manufacturability, facilitates servicing and replacement of the parts, and usually improves the overall aesthetics.

FIG. 7 shows the specialized mechanical support (38) appearing in FIGS. 2 and 4. This specialized mechanical support (38) is used firstly to fix the optical switches as explained hereafter. Secondly, the specialized mechanical support (38) is used to facilitate the transition between the part of a cable (not shown) between the relatively fixed section of the prosthesis (10) and the relatively movable section thereof.

Connectors (78), attached to the brackets (42) of the knee member (12), provide the required connections. A similar connector (78) is provided on the motor (70). A two-part wire clamp (39A, 39B) on parts (254) allows to hold the wire on the support (38).

Control System

Figure 14:
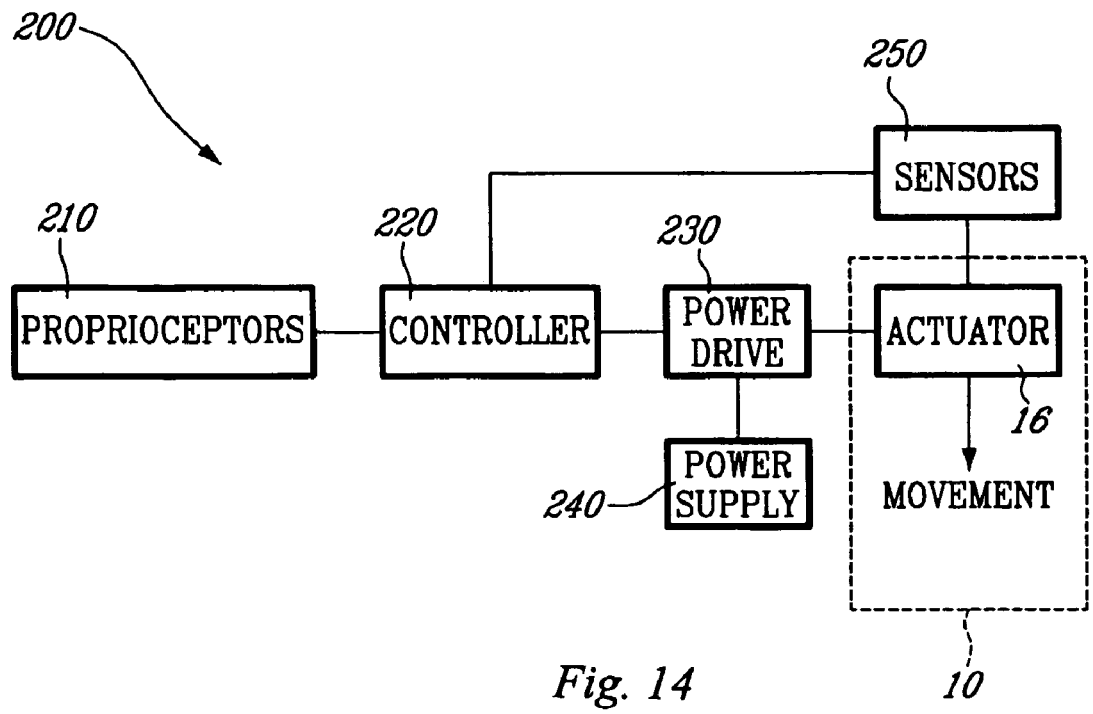
FIG. 14 is a bloc diagram showing an example of a control system for the actuator of the prosthesis.

The actuator (16) shown in the prosthesis of FIGS. 1 to 7 is controlled by the control system (200) shown in FIG. 14. This figure first shows a set of artificial proprioceptors (210), which are sensors used to capture information in real time about the dynamics of the amputee's locomotion. The set of artificial proprioceptors (210) provide sensing information to a controller (220). The controller (220) determines the joint trajectories and the required forces that must be applied by the actuator (16). The set-point (joint trajectories and the required forces) is then sent to the actuator (16) via the power drive (230) itself connected to the power supply (240).

The power supply (240) can be, for example, a flexible battery pack belt such as the Lighting Powerbelt model, manufactured by Cine Power International Ltd. Other examples of power supply (240) are the battery model SLPB526495 manufactured by Worley Inc. and the super capacitors manufactured by Cap-XX. Examples of power drive (230) are the 5121 model, manufactured by Copley Controls Corps Inc. and the model BE40A8 manufactured by Advanced Motion Control. It should be noted that the design of the power supply (240) and that of the power drive (230) are not limited to the devices mentioned here above and could be performed by any custom or commercial products if the selected devices meet the electrical specification of the selected actuator (16) used with the prosthesis (10).

Preferably, the prosthesis (10) further includes a set of sensors (250) to provide feedback information to the controller (220). This feedback allows the controller (220) to adjust the forces and various other parameters. Examples of parameters that can be monitored are the relative angle of the knee member (12) and the torque at the knee member (12) being exerted by the actuator (16). Other types of measurements may be taken. The measurement of the relative angle of the knee member (12) can be taken, for example, by a standard commercially available incremental optical encoder (260) such as a reading head model EM1-0-250 and a Mylar® strip (262) marked with evenly spaced increments model LIN-250-16-S2037 manufactured by US Digital Inc. Others sensors used as limit switches for the limitation of the angular motion of the prosthesis (10) are the optical switches preferably mounted onto the specialized mechanical support (38). Cable connectors (78), shown in FIGS. 1 and 2, allow to link the external devices to internal components of the prosthesis (10).

The optical switches (252) are fixed on the first pivot axis (31) and are used to set the reference angular position of the knee member (12). Once this reference position is known, the optical encoder information is used to compute the knee member (12) angle via motor rotation, roller-screw pitch and prosthesis geometry. Moreover, the optical switches (252) are used to prevent out of range motion by sending a signal to the controller (220) when the knee member (12) approaches critical positions. Of course, the optical switches (252) may be use for other purposes according to the nature of the command associated with the switches detection. Another possible way of measuring the relative angle of the knee member (12) is by using a combination of an absolute optical encoder such as, for example, encoder model E2-512-250-i manufactured by US Digital Inc. and optical switches. An example of these switches is the switch model PM-L24 manufactured by SUNX.

The measurement of the torque is taken from the force being exerted by the actuator (16) measured by a load cell (92). An example of the load cell is the model LC 202 1 K manufactured by Omegadyne. A connector on the motor (70) links the internal sensor to the cable. It should be noted that the sensors (250) of the prosthesis (10) are not limited to the above-mentioned devices and can be performed by other suitable instruments.

Operation of the Front Actuator Configuration

In operation, the knee assembly (12) is connected to the socket (18) and the pivot assembly (30) permits relative motion between the trans-tibial member and the knee about a generally transverse horizontal axis. Rotation of the knee member relative to the trans-tibial member (14) is controlled by operation of the actuator (16). The actuator (16) acts between the pivot assembly (80) on the knee member (12) and the pivot assembly (100) at the lower end of the trans-tibial member (14) so that changes in the length of the actuator (16) will cause a corresponding rotation about the pivot (30).

The length of the actuator (16) is adjusted by control signals from the controller (220) that supplies power to the motor (70) to rotate the screw (72) in one direction or the other. Rotation of the screw (72) causes the follower (74) to move along the screw (72) and this motion is transferred through the connection provided by the pivot assembly (100) to the trans-tibial member (14). This causes a corresponding rotation of the knee member (12) and trans-tibial member (14) about the pivot axis (30) to provide the desired motion. Obviously the rate and extent of rotation may be adjusted through control signals to the motor (70) and the sensors embodied in the prosthesis provide the feedback to the controller (220).

Rear Actuator Configuration

FIGS. 8 to 13 show the prosthesis (10) in accordance with a second possible embodiment. This illustrates an example of a prosthesis (10) with a rear actuator configuration. This embodiment is very similar to the one using the front actuator configuration. It is illustrated with another kind of actuator (16) and another model of artificial foot (20). The middle section (14B) of the trans-tibial member (14) uses four bars (54) instead of two. It does not have a back plate. Moreover, no bottom extension is provided on the trans-tibial member (14).

The trans-tibial member (14) also has a shell type architecture composed, for example, of ½" trans-tibial post bars (54) linking together the knee member (12) and the artificial foot (20). In the illustrated embodiment, the actuator (16) could be a standard linear motor (FIG. 5) or a serial elastic actuator (SEA) (FIG. 8) equipped with a customized commercially available motor (70) although the prosthesis (10) is designed such that it can receive any type of linear actuator (16) of the same approximate size. The SEA actuator (16) (FIG. 8) has a ball screw transmission system including a screw (72) coupled with an elastic device (110) of known characteristics. This actuator (16) (FIG. 8) allows a force control actuation based on the deformation of elastic components. As well, the design allows energy storage, shock tolerance and relatively stable force control. The SEA actuator (16) (FIG. 8) was developed by Gill Pratt of the MIT Leg Laboratory and has been patented in 1997 as U.S. Pat. No. 5,650,704. In one implementation, it was provided with a Litton BN23-28 motor (70) and a ⅜" diameter with ⅛" pitch ball screw (72). The SEA actuator (16) (FIG. 8) is commercialized by Yobotic Inc.

Figure 8:
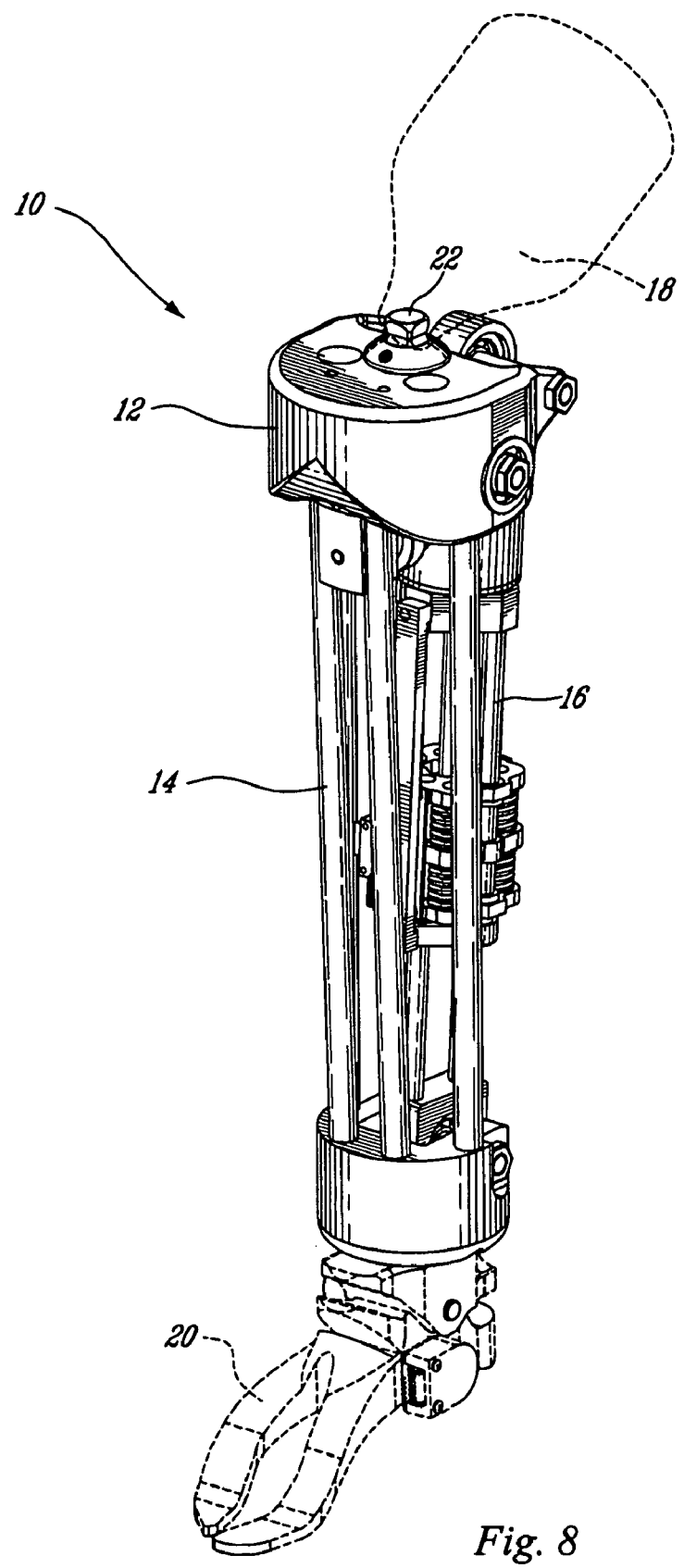
FIG. 8 is a perspective view of an actuated prosthesis with a rear actuator configuration, in accordance with another possible embodiment of the present invention.
Figure 9:
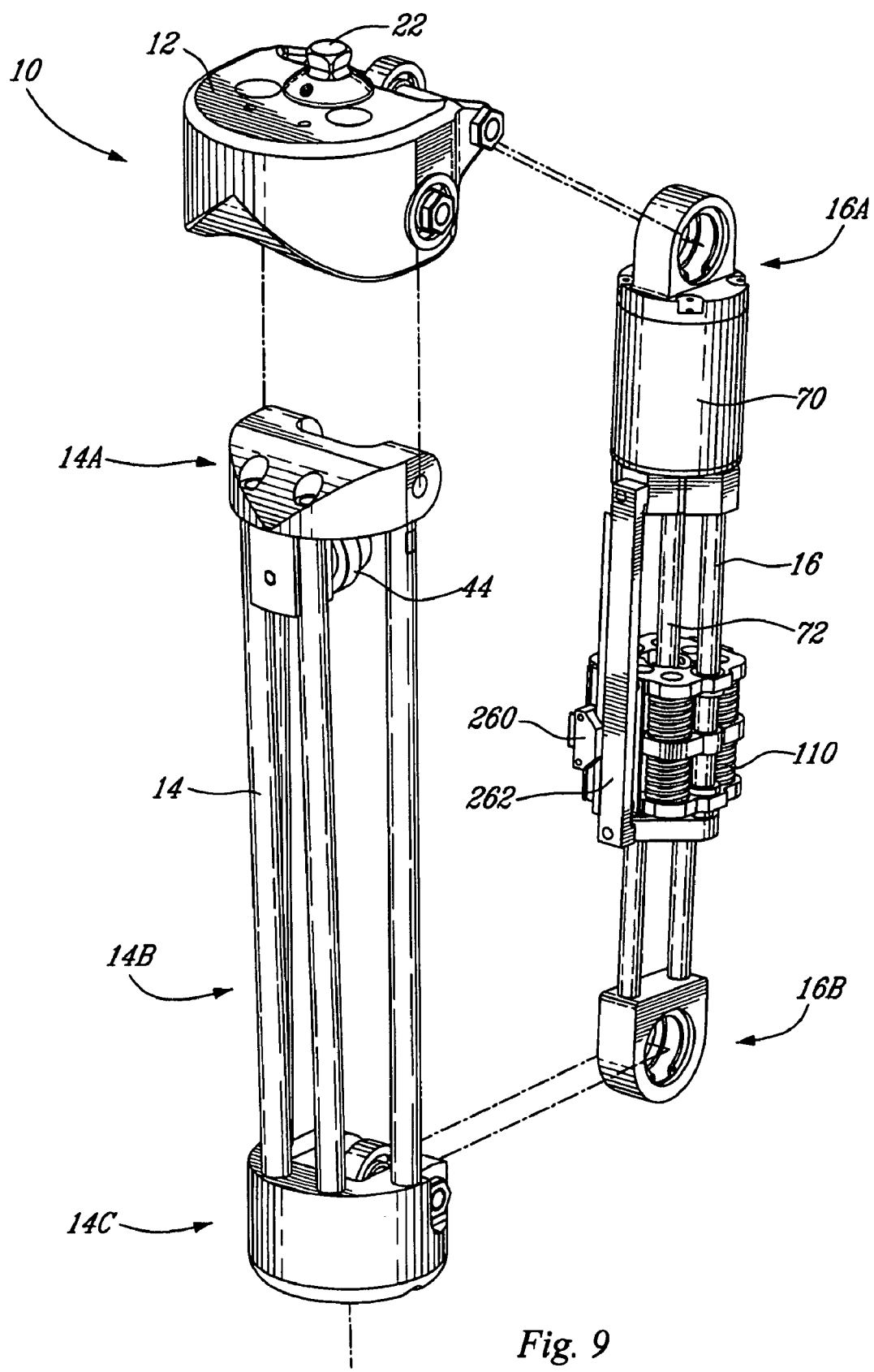
FIG. 9 is a partially exploded perspective view of the prosthesis shown in FIG. 8.
Figure 10:
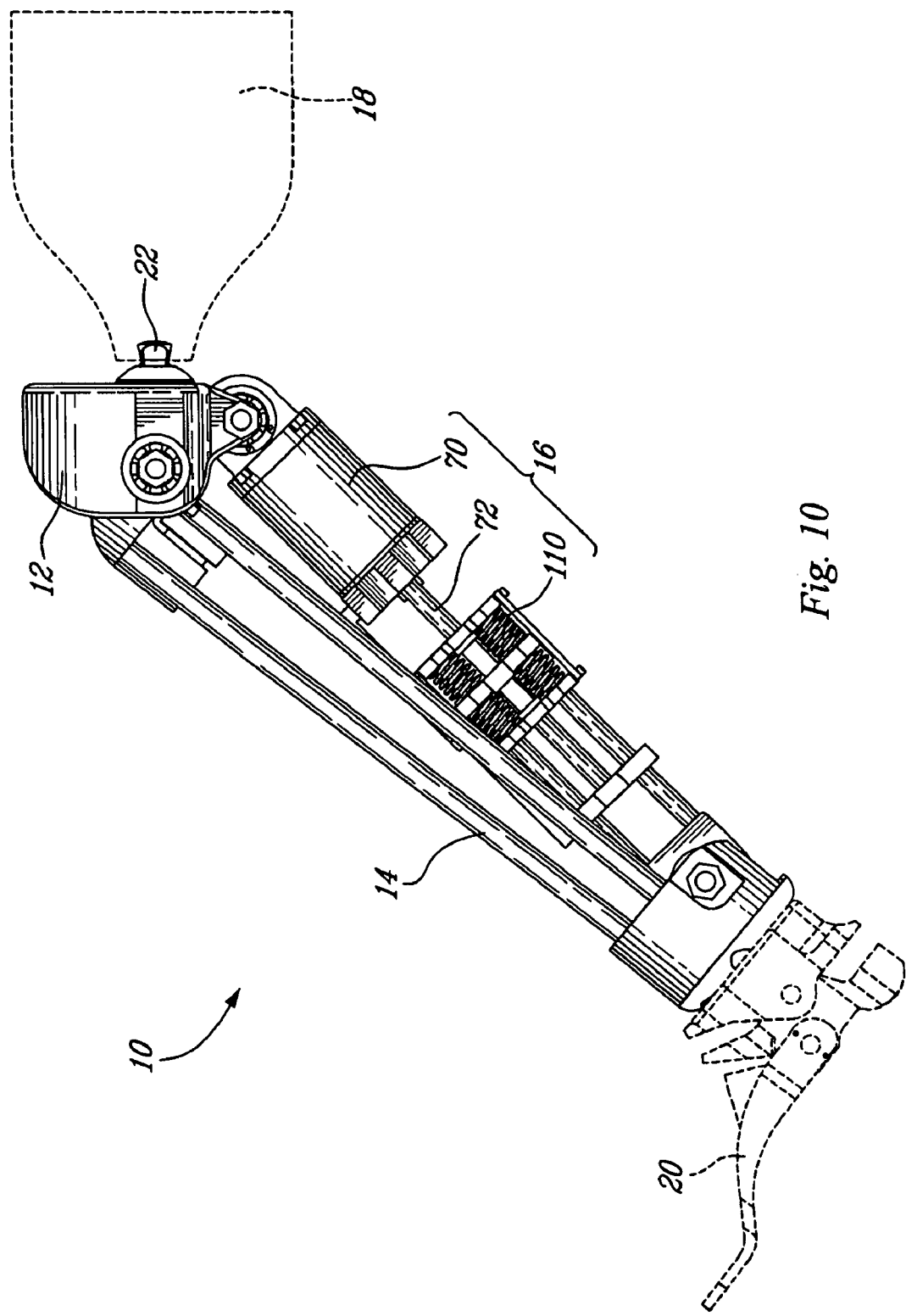
FIG. 10 is a side view of the prosthesis shown in FIG. 8.
Figure 11:
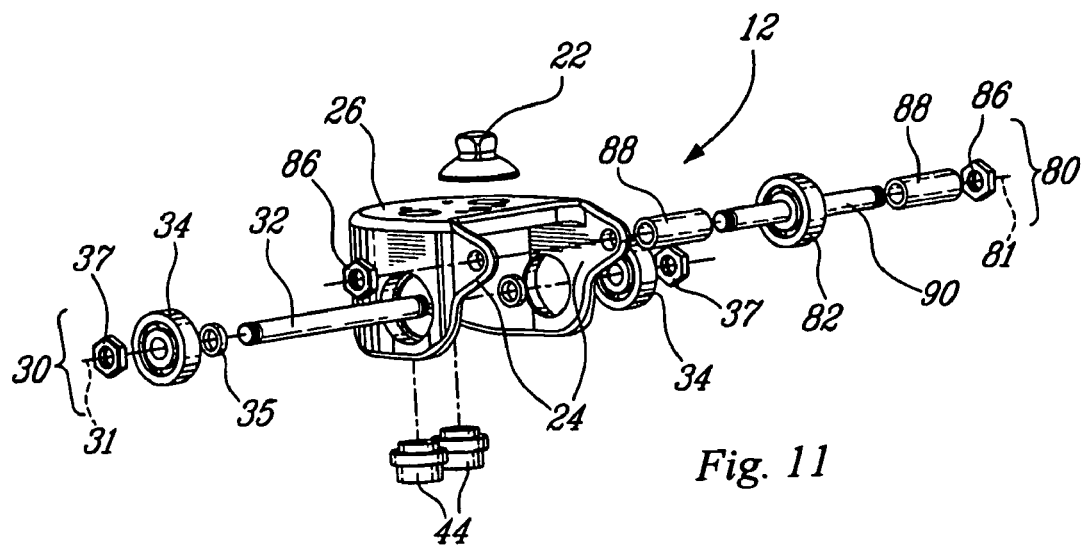
FIG. 11 is an exploded perspective view of the knee member, the first pivot assembly and the second pivot assembly shown in FIG. 8.
Figure 12:
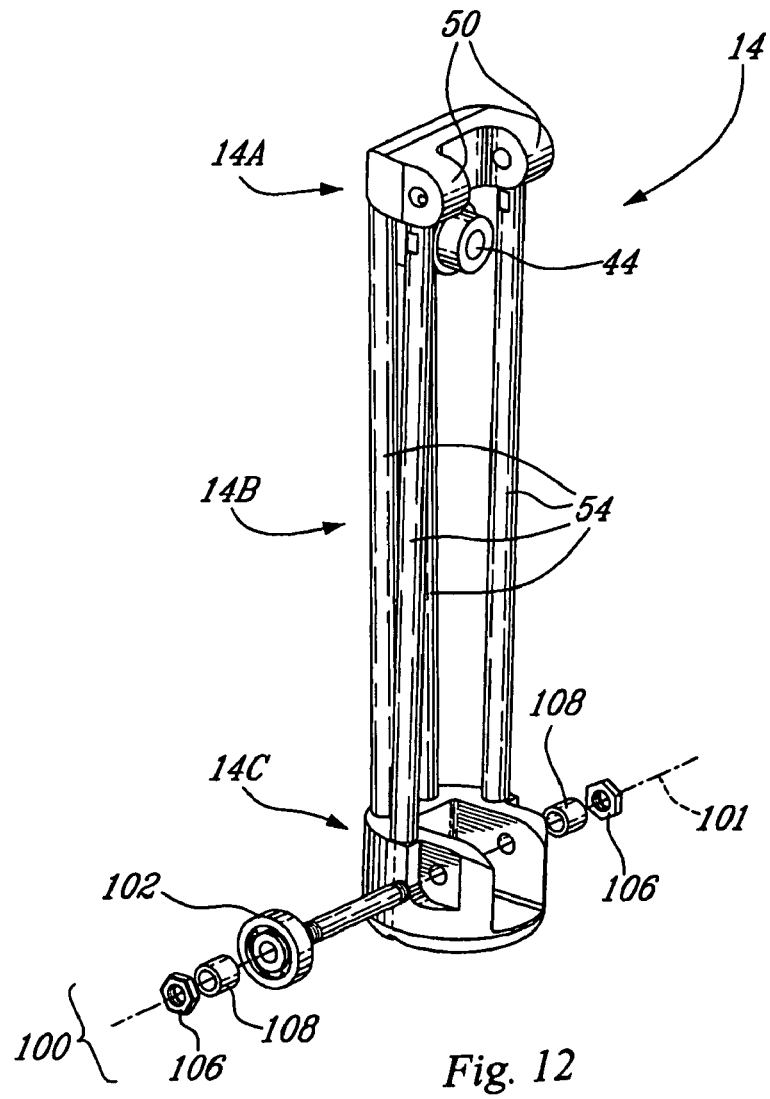
FIG. 12 is a partially exploded view of the trans-tibial member and the third pivot assembly shown in FIG. 8.

In the arrangement shown in FIG. 8, the torque may be measured, for example, by a standard commercially available potentiometer measuring the compression of the elastic devices of the actuator (16) such as the conductive plastic resistance elements model PTN025 manufactured by Novotechnik Inc. The measurement of the angle between the knee member (12) and trans-tibial member (14) can also be computed directly from the measurement of the length of the actuator (16) and the known geometry of the prosthesis. A standard commercially available incremental optical encoder (260), such as reading head model EMI-0-250 is mounted on the moveable part and a Mylar strip (262) marked with evenly spaced increments (model LIN-250-16-S2037 manufactured by US Digital Inc.) is secured to the stationary part. As the motor (70) rotates the drive screw (70), a direct reading of the length of the actuator (16) is thus obtained.

Figure 13:
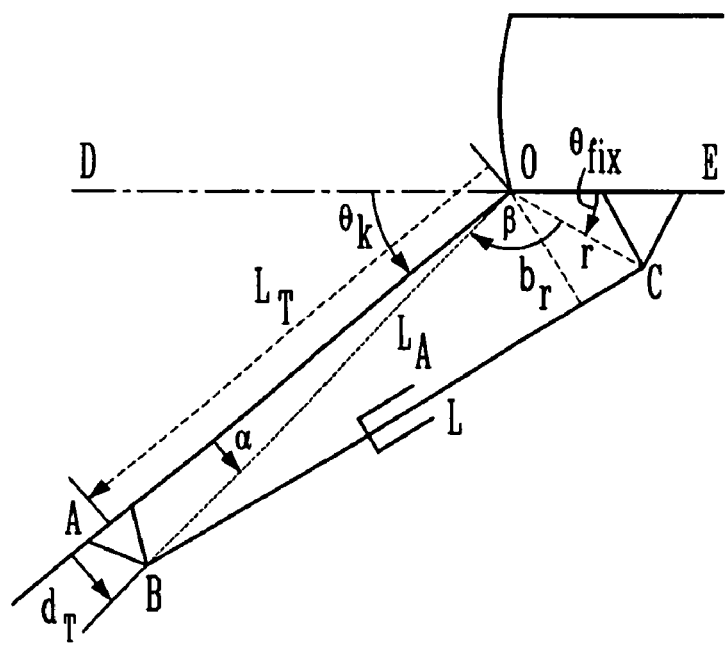
FIG. 13 is a diagram illustrating the geometrical model with the rear actuator configuration.

FIG. 13 illustrates the geometrical model of the rear actuator configuration. It is essentially similar to that of the front actuator configuration as shown in FIG. 6.

Inverted Actuator

In each of the above embodiments, the actuator (16) has been arranged with the motor (70) adjacent to the knee member (12) and the follower (74) extending to the lower, ankle region of the trans-tibial member (14). Such an arrangement simplifies the routing of the power and control lines and generally allows a tapering profile toward the ankle to conform to the natural profile of a leg. However, with these arrangements the motor (70) moves with the pivot assembly (80) through the range of motion of the prosthesis and accordingly the swept volume of the motor must be accommodated in the design of the knee member (12). Similarly, the location of the motor (70) adjacent the knee member causes variations in the mass distribution and hence the dynamics of the prosthesis during movement of the leg which may result in an unnatural feel to the prosthesis in use. To address these considerations a further embodiment of the prosthesis (10) is shown in FIGS. 15 to 21 in which like components will be described by like reference numerals with a prime suffix (') for clarity.

Figure 15:
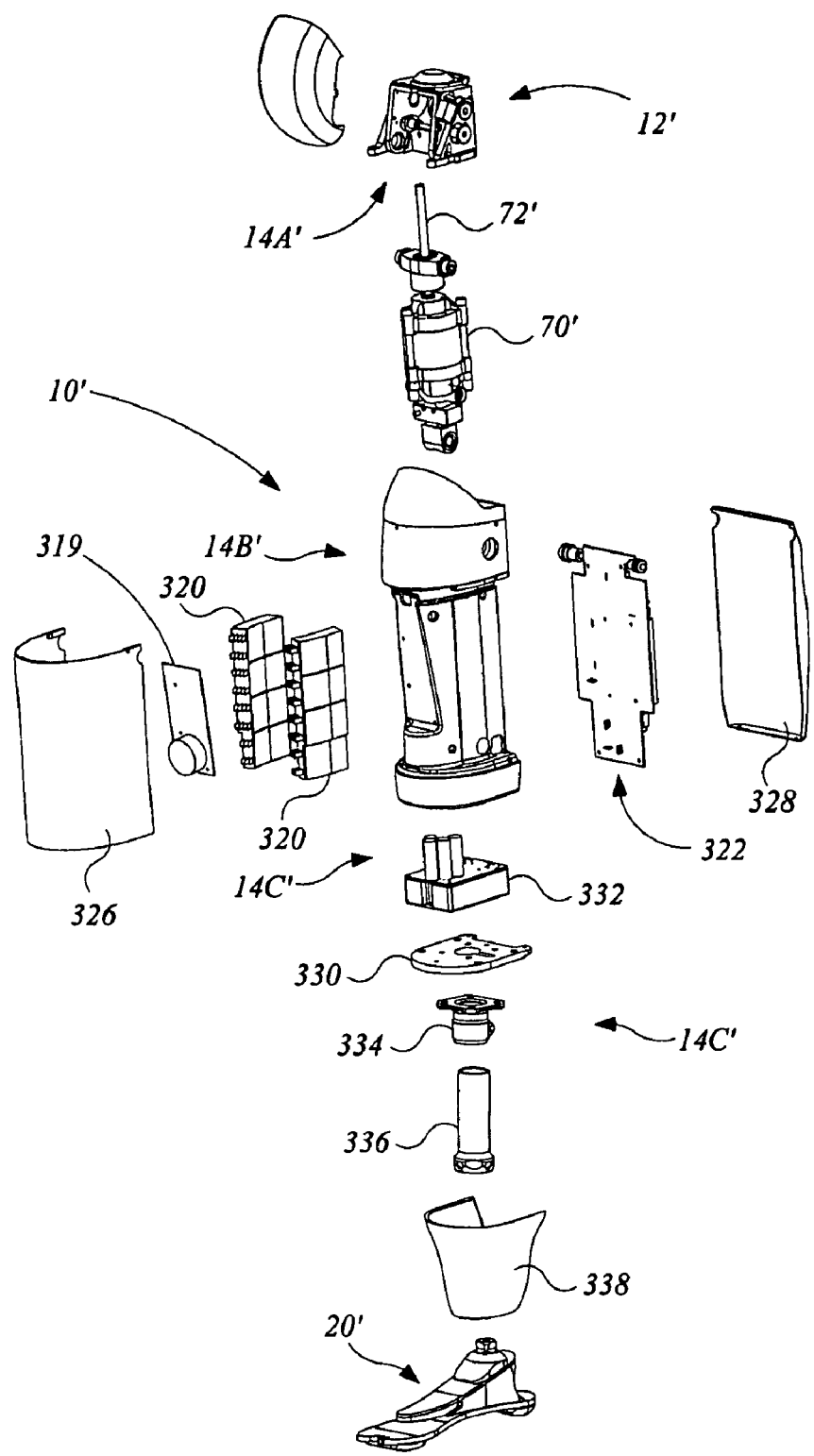
FIG. 15 is an exploded perspective view of a further embodiment of a prosthesis.
Figure 16:
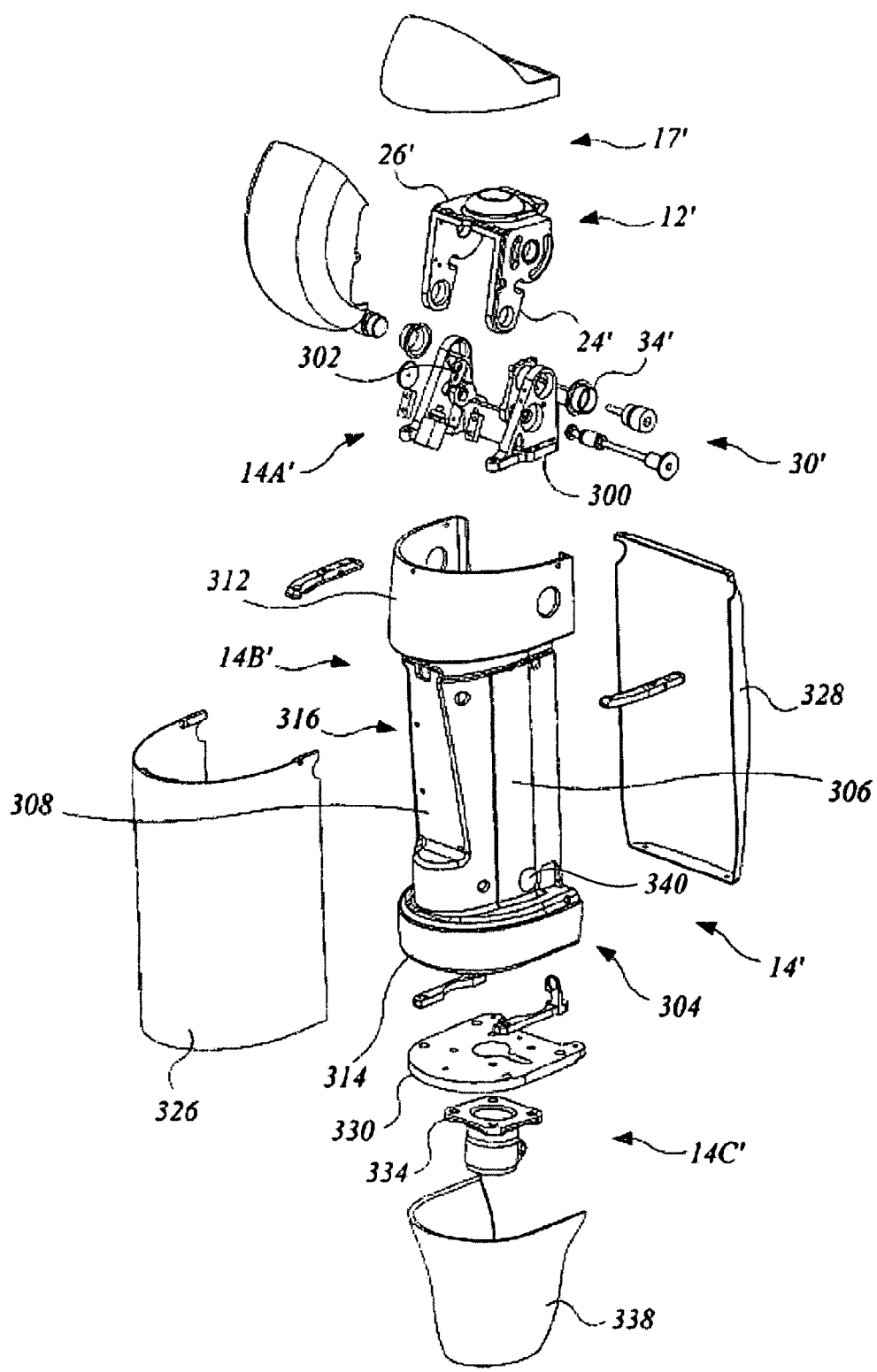
FIG. 16 is a view similar to FIG. 15 on an enlarged scale of structural components of the prosthesis of FIG. 15.
Figure 18:
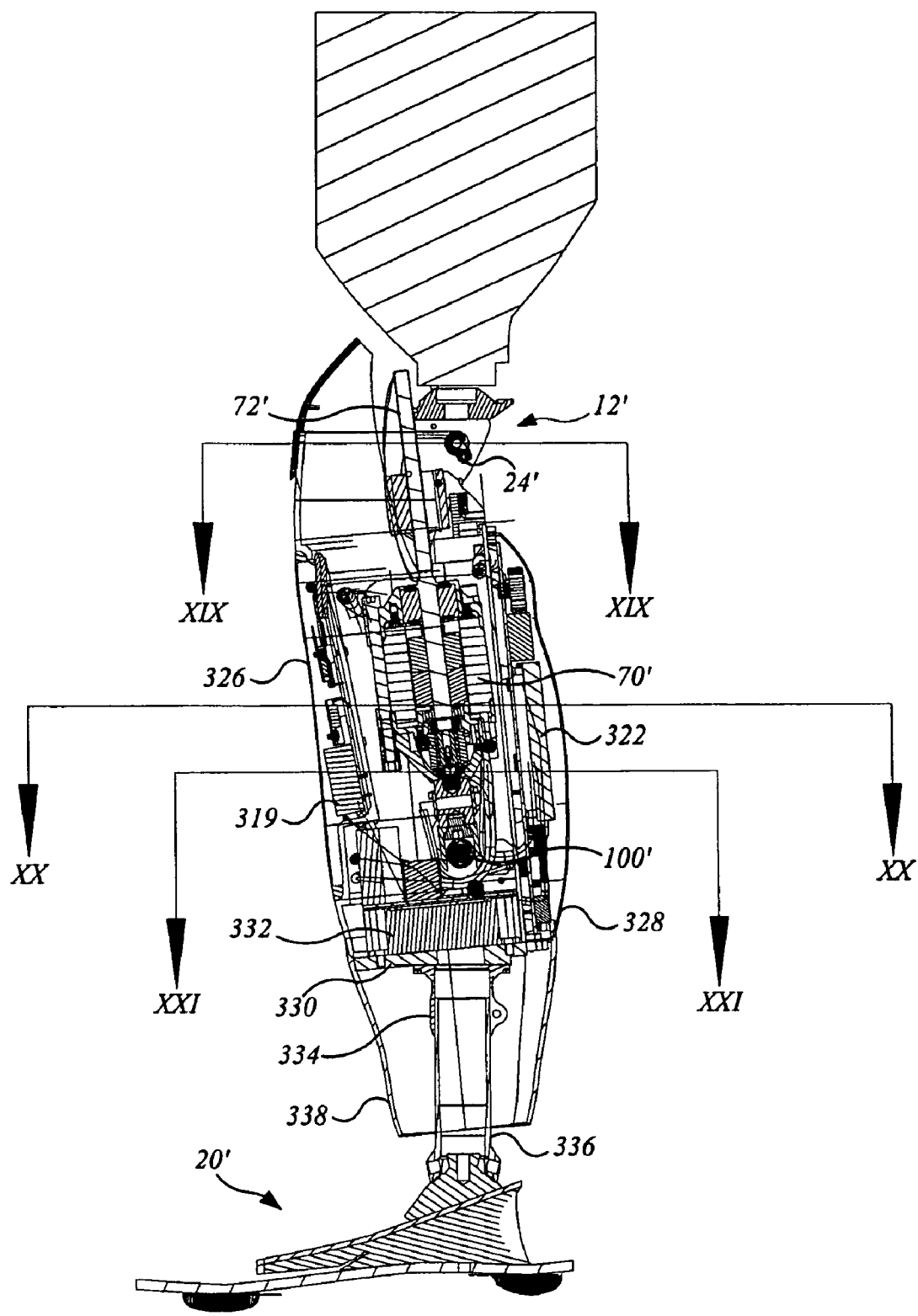
FIG. 18 is a longitudinal side section of the prosthesis of FIG. 15.
Figure 19:
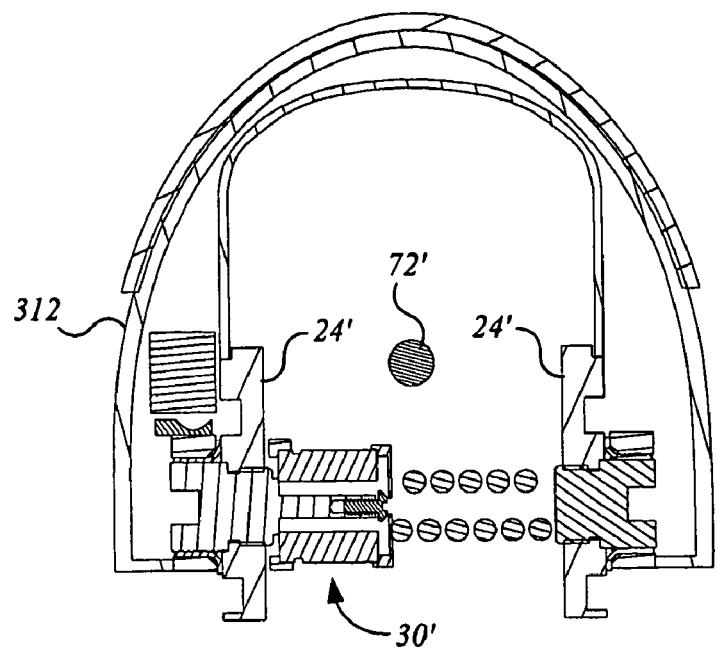
FIG. 19 is a view on the line XIX-XIX of FIG. 18.
Figure 20:
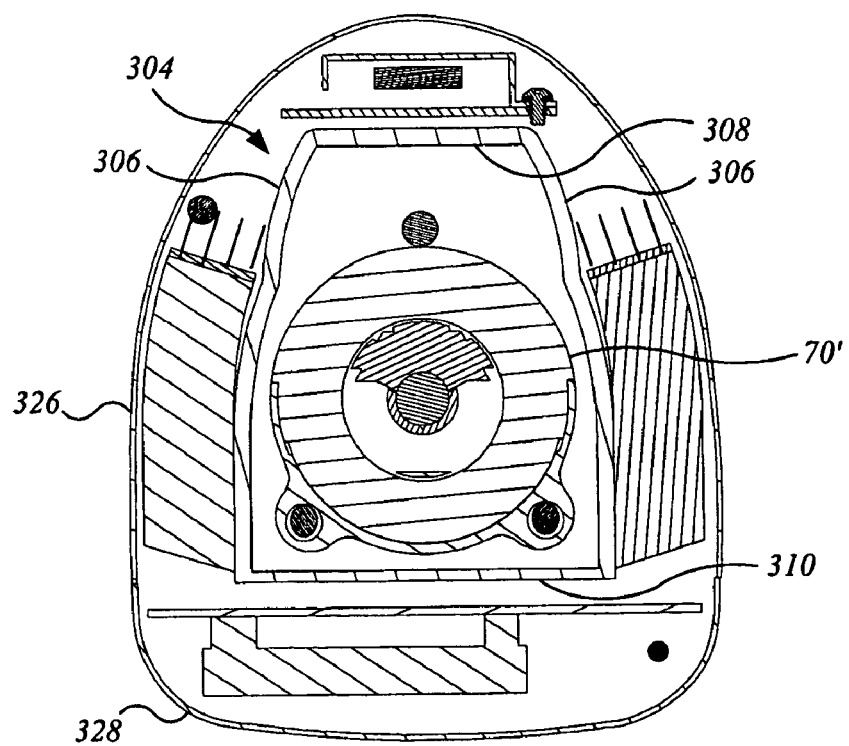
FIG. 20 is a view on the line XX-XX of FIG. 18.
Figure 21:
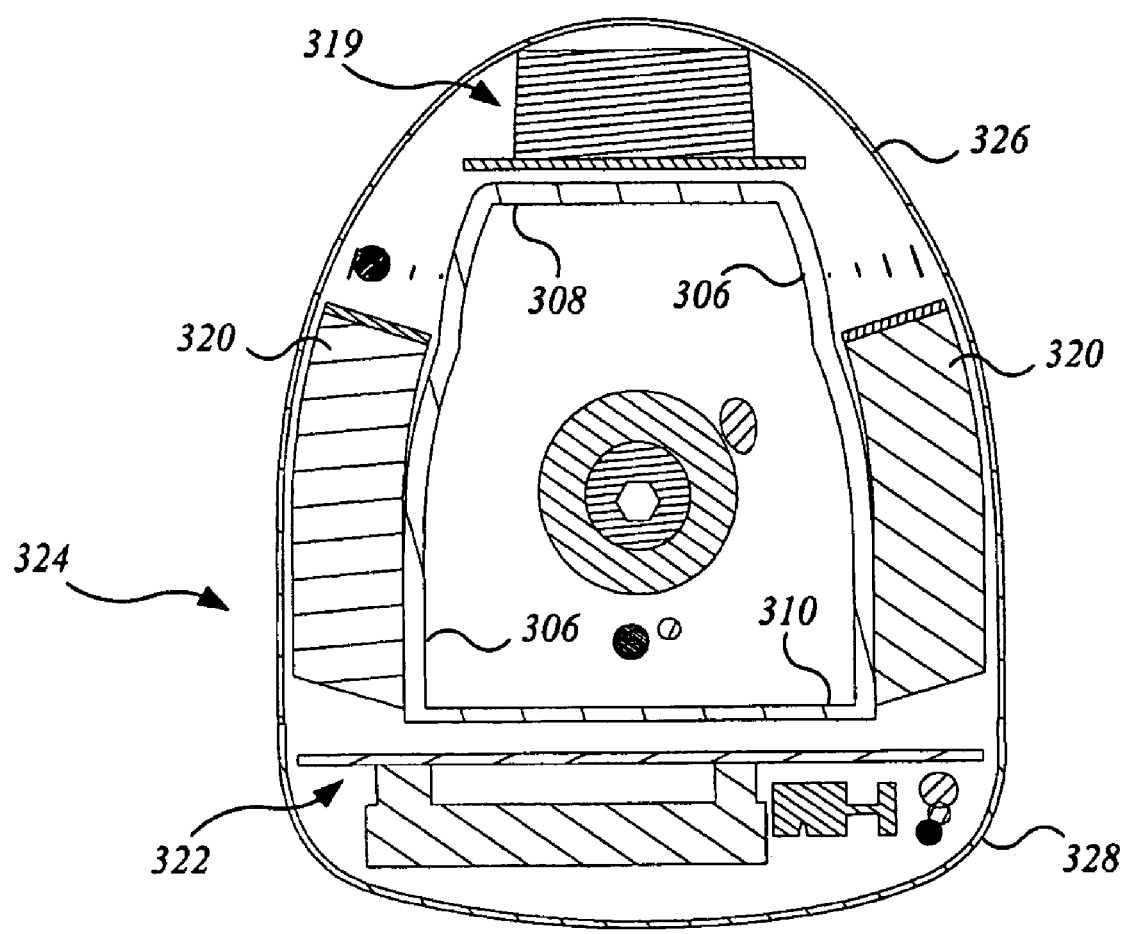
FIG. 21 is a view on the line XXI-XXI of FIG. 18.

Referring therefore particularly to FIGS. 15 and 18, a prosthesis (10') has a knee member (12)' formed as a U shaped member with flanges (24') extending from the upper plate (26'). The lower ends of the flanges (24') receive respective bearings (34') forming part of the pivot assembly (30') that connects the knee member (12') to the trans-tibial member (14'). A socket connector assembly (17') is secured to the upper plate (26') for connection to an appropriate socket.

The trans-tibial member (14') has an upper section (14A') formed by a pair of spaced webs (300) with bores (302) to receive the bearings (34') of the pivot assembly (30'). The webs (300) are secured to shoulders, not shown, at the upper end of the middle section (14B'). The middle section (14B') is formed as an open channel member (304) with laterally spaced side walls (306) interconnected by an integrally formed front wall (308). The channel member (304) is closed by a back wall (310), which is removable to permit access to the interior of the channel member (304). The middle section (14B') thus provides a lightweight structural member of high torsional and bending strength to meet the loading placed upon it.

The upper and lower ends (312, 314) respectively of the channel member (304) are enlarged to receive the upper section (14A') and lower section (14B') and thereby define a waisted intermediate portion (316). The side walls (306) in the waisted portion (316) have generally planar flanks that support energy storage modules (320), typically battery packs, on either side of the channel member (304). The front wall (308) is also formed with a planar facet (314) to receive a control board (319) associated with the operation of the actuator (16') and to regulate power flow to and from the energy storage modules (320).

The back wall (310) also serves as a mounting point for a further control board (322) utilized in the control of the actuator (16'). An external shell (324), formed from front and rear sections (326, 328) respectively, encompasses the intermediate portion (316) and is supported on the enlarged upper and lower ends (312, 314). The shell (324) protects the components mounted on the waisted intermediate portion (316) as well as being contoured to conform to the appearance of a human leg.

The lower section (14C') of the trans-tibial member (14') includes a mounting plate (330) received within the enlarged lower end (314). The plate (330) is bolted the lower ends (314) of the channel member (304) and to the power drive (322) utilized in the control of the actuator (16') which in turn is secured to the middle section (14B)'. A socket (334) is mounted on the underside of the plate (330) to receive a tubular member (336) of the foot connector assembly (20'). The tubular member (336) extends to a male socket formed on the foot (20') and its length may be adjusted to tailor the prosthesis to a particular individual. A skirt (338) extends around the tubular member (336) for cosmetic considerations.

Figure 17:
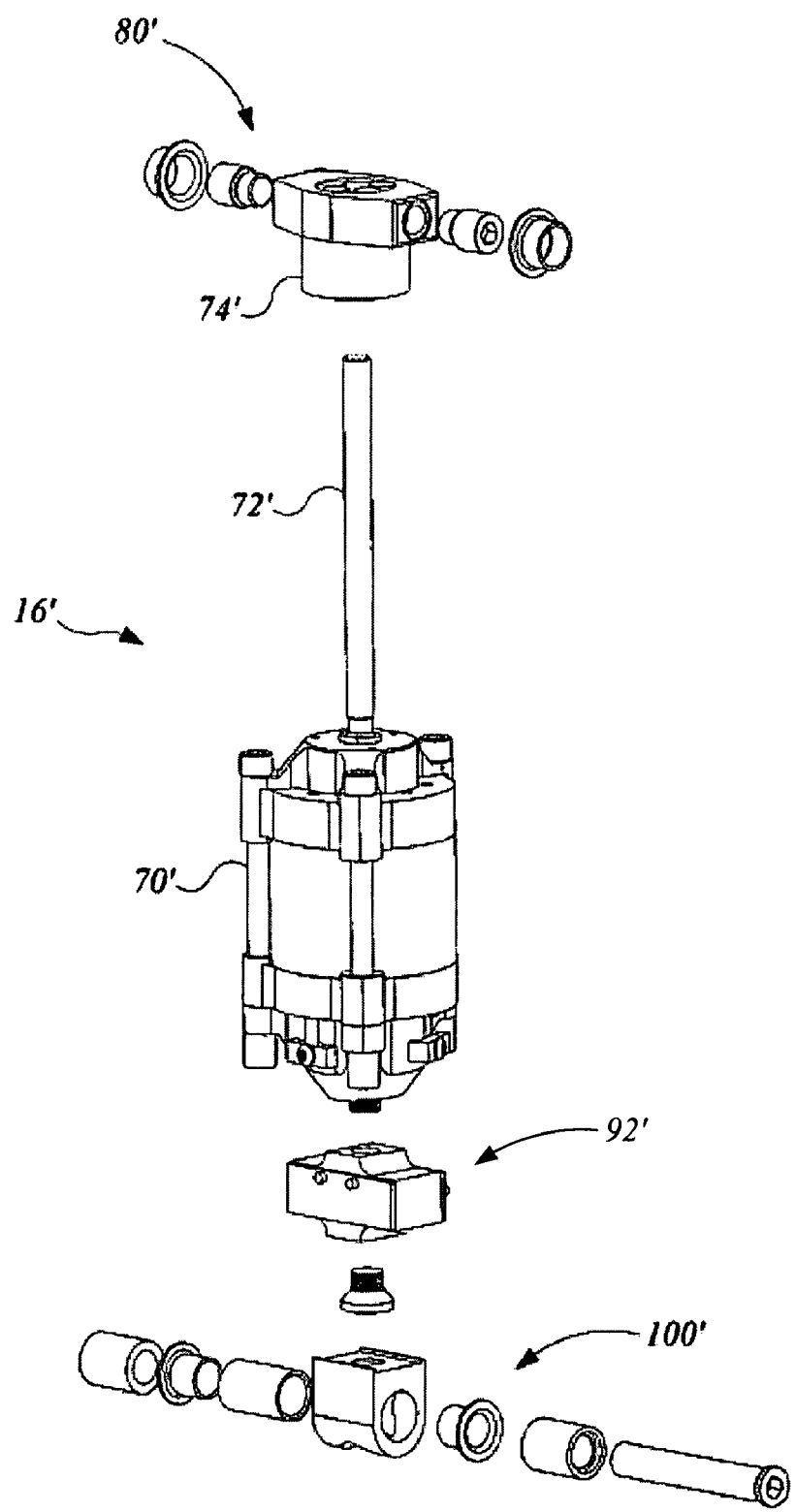
FIG. 17 is a view similar to FIG. 15 on an enlarged scale of the motive components of the prosthesis of FIG. 15.

As can best be seen in FIGS. 15 and 17, the actuator (16') includes a motor (70') with a screw (72'). The actuator (16') is located within the interior of the middle section (14B') so as to be surrounded by the walls (308, 310, 312), with the screw (72') extending beyond the upper end (312) and between the flanges (26') of the knee member (12'). The screw (72') engages a follower (74') forming part of the pivot assembly (80') that is connected to the knee member (12') at a location spaced from the pivot assembly (30').

The motor (70') is similarly connected through a pivot assembly (100') to the lower end (314) of the middle section (14B') at mounting points (340) (FIG. 16) that receive the bearings of the pivot assembly (100').

Operation of Inverted Actuator

The operation of the inverted actuator is essentially the same as that of the front mounted actuator with rotation of the motor (70') causing a change in the effective length of the actuator (16') and a corresponding rotation of the knee member (12') relative to trans-tibial member (14'). During such rotation it will be noted that the motor (70') swings about its pivot assembly (100') but does not translate along the axis of the prosthesis (10'). The swept volume of the motor through the range of movement is thus reduced allowing better utilisation of the space available. It will also be noted that the mass distribution in the prosthesis remains substantially uniform in view of the lack of translation of the motor to provide a more natural feel to the operation of the prosthesis.

The integration of the energy module and control boards on the middle section also provides a more self contained unit and simplifies the routing of the control and power transmission.

EXAMPLE

Calculation for the Optimal Angle

One can assume the following technical specifications:
a geometrical volume corresponding to the anthropometrical volume of a natural shank of an individual having a weight of 70 kg and a height of 170 cm;
a maximal distance r set at 0.055 m, that is r<0.055 m;

a minimal and a maximal length $L_T$ set at 0.3 m and 0.4 m respectively, that is 0.3 m<$L_T$<0.4 m; and a minimal and a maximal distance $d_T$ set at −0.015 m and +0.015 m, that is −0.015 m<$d_T$<+0.015 m.

The geometrical model can be defined with the following equations:

$$\beta = \pi - \theta_{fix} - \alpha - \theta_K \qquad \text{Equation 1}$$

$$L_A = \sqrt{L_T^2 + d_T^2} \qquad \text{Equation 2}$$

$$\alpha = \arctan\left(\frac{d_T}{L_T}\right) \qquad \text{Equation 3}$$

$$L^2 = L_A^2 + r^2 - 2 \cdot L_A \cdot r \cdot \cos\beta \qquad \text{Equation 4}$$

$$b_r = \frac{r \cdot L_A \cdot \sin\beta}{\sqrt{L_A^2 + r^2 - 2 \cdot L_A \cdot r \cdot \cos\beta}} \qquad \text{Equation 5}$$

where $\theta_K$ Knee angle, ∠DOA r Distance between the center of rotation "O" of the knee member (12) and the attachment point of the actuator (16) on the knee member (12)

$\theta_{fix}$ Angle between r and the stump's center axis, ∠EOC $L_A$ Distance between the center of rotation of the knee member (12) and the attachment point of the actuator (16) on the trans-tibial member (14) $\overline{OB}$ $L_T$ Length between the center of rotation of the knee member (12) and the attachment point of the trans-tibial member (14) $\overline{OA}$ $d_T$ Distance between the center axis of the trans-tibial member (14) and the actuator (16) attachment point of the trans-tibial member (14), $\overline{AB}$ $\alpha$ Angle formed between $L_T$, $L_A$: ∠AOB L Length of the actuator (16), $\overline{BC}$ $\beta$ Angle formed between $L_A$, r: ∠BOC $b_r$ Lever arm of the actuator (16) versus the first pivot axis (31)

Preferably, the lever arm br is assumed to be maximum at a knee angle $\theta_k$ of 35 degrees. The geometrical calculation of the mechanical design are based on the setting of the distance r, the length $L_T$, the distance $d_T$ and the angle $\theta_{fix}$. Therefore, these parameters are defined in accordance with the anthropomorphic measurements of the amputee and the selected actuator (16).

For an angle $\theta_{fix}$, the optimal value for a maximum lever arm $b_r$ is found when Equation 5 is at a maximum value, that is:

$$\frac{\partial b_r}{\partial \theta_{fix}} = 0 \qquad \text{Equation 6}$$

where $\theta_{fix} = \pi - \pi - \theta_K - \beta$

This condition is reached for the configuration shown in FIGS. 6 and 13 when:

$$\beta = \pm \frac{3}{2}\pi \qquad \text{Equation 7}$$

From Equation 1, the optimal angle between distance r and the center axis of the socket, denoted $\theta_{fix}|_{optimal}$, is defined as:

$$\theta_{fix}|_{optimal} = \begin{bmatrix} +\pi/2 \\ -\pi/2 \end{bmatrix} - \theta_k - \alpha \qquad \text{Equation 8}$$

where $+\pi/2$ and $-\pi/2$ correspond to the rear and the front actuator configuration respectively.

The result is that the optimal angle $\theta_{fix}$ is preferably set at 125±3 degrees.

It will be appreciated that alternative dimensions and parameters would apply to other limbs such as an arm but the adaptation of the basic components described above to such an environment could readily be made once the underlying concepts are understood.

What is claimed is:

1. An actuated leg prosthesis for replacement of a leg of an above knee amputee, the prosthesis comprising:
    a knee member;
    a socket connector assembly for connecting a socket to said knee member;
    a trans-tibial member having opposite top and bottom ends spaced apart along a main longitudinal axis;
    a connector assembly for connecting an artificial foot to said bottom end of said trans-tibial member;
    a first pivot assembly for operatively connecting said top end of said trans-tibial member to said knee member to permit relative rotation between said knee member and said trans-tibial member about a first pivot axis defined by said pivot assembly; and
    a linear actuator comprising a rotary motor, a screw rotatable by said rotary motor and a follower displaceable along said screw upon rotation thereof by said rotary motor, said rotary motor being pivotally connected to said trans-tibial member via a second pivot assembly defining a second pivot axis and said follower being pivotally connected to said knee member at a location spaced from said first pivot assembly and thereby defining a third pivot axis,
    wherein said first pivot axis is a prosthetic knee joint, wherein during locomotion, rotation of said rotary motor rotates said screw in or out of said follower thereby causing a corresponding rotation of said knee member relative to said trans-tibial member about said first pivot axis and wherein relative rotation between said knee member and said trans-tibial member is about said first pivot axis only, relative rotation between said linear actuator and said trans-tibial member is about said second pivot axis only, and relative rotation between said linear actuator and said knee member is about said third pivot axis only.

2. The prosthesis according to claim 1, wherein said actuator is connected to said knee member and said trans-tibial member by respective pivotal connections having pivot axes substantially parallel to and spaced from said first axis.

3. The prosthesis according to claim 1, wherein said actuator is located within said trans-tibial member.

4. The prosthesis according to claim 3 wherein said trans-tibial member includes a hollow shell and said actuator is located within said shell.

5. The prosthesis according to claim 4 wherein said shell is formed from an open channel member and a detachable closure.

6. The prosthesis according to claim 4 wherein an energy storage module is supported on said shell.

7. The prosthesis according to claim 4 wherein a circuit board is supported on said shell.

8. The prosthesis according to claim 3, wherein said trans-tibial member includes a back plate extending between said top and bottom ends thereof.

9. The prosthesis according to claim 1, further comprising an artificial foot attached to said connector assembly, said artificial foot defining a front side and a rear side of the prosthesis.

10. The prosthesis according to claim 9, wherein one end of said actuator is connected to said knee member forwardly of said first pivot axis.

11. The prosthesis according to claim 9, further comprising a socket attached to said knee member.

12. The prosthesis according to claim 1, further comprising a controller for controlling said actuator.

13. The prosthesis according to claim 12, wherein said controller outputs control signals to said actuator in response to input signals from proprioceptors.

14. The prosthesis according to claim 13, wherein the controller has an output connected to a power drive, the power drive supplying electrical energy to said actuator, from a power source, in response to the control signals.

15. The prosthesis according to claim 13, wherein the input signals further comprise signals from sensors mounted on said actuator.

16. The prosthesis according to claim 1 wherein a load sensor is interposed between said actuator and one of said members to provide an indication of loads imposed on said prosthesis.

17. The prosthesis according to claim 1 including a sensor to provide an indication of relative motion between said knee member and said trans-tibial member.

18. The prosthesis of claim 17 wherein said sensor is an optical sensor.

19. The prosthesis of claim 1, wherein said knee member comprises an integral u-shaped member with flanges downwardly extending from an upper top plate.

20. The prosthesis of claim 19, wherein said socket connector assembly provides for connecting said socket to said upper top plate of said knee member.

21. The prosthesis of claim 19, wherein said first pivot assembly operatively connects said top end of said trans-tibial member to said flanges of said knee member.

22. The prosthesis of claim 1, wherein said trans-tibial member comprises an open channel member between said top and bottom ends thereof having spaced apart walls, said second pivot assembly being pivotally mounted to said spaced apart walls of said open channel member.

* * * * *

UNITED STATES PATENT AND TRADEMARK OFFICE
CERTIFICATE OF CORRECTION

PATENT NO. : 7,736,394 B2  
APPLICATION NO. : 10/721764  
DATED : June 15, 2010  
INVENTOR(S) : Stephane Bedard et al.

Page 1 of 2

It is certified that error appears in the above-identified patent and that said Letters Patent is hereby corrected as shown below:

In Column 1, Line 10 (Approx.), Change "2002 ;" to --2002;--.

In Column 1, Line 11 (Approx.), Change "2002 ;" to --2002;--.

In Column 2, Lines 9-10, After "member;" delete "a socket connector assembly for connecting a socket to said primary joint member;" and insert the same on Line 10, Col. 2 as a new paragraph.

In Column 3, Line 51, Delete "FIGS. 15 to 21 show the inverted actuator configuration." and insert the same on Line 50, Col. 3 after "configuration." as a continuation of the paragraph.

In Columns 4-5, Lines 63-67 (Col. 4) and 1-2 (Col. 5), Delete "These bumpers (44) can be, for example, bumper model GBA-1 manufactured by Tecspak Inc. Of course, other types of bumpers (44) may be used as well. They are mounted on corresponding brackets (42) located on the side and the front of the upper plate (26) of the knee member (12). The brackets (42) are also used to support connectors (78) which are described later in the description." and insert the same on Line 62, Col. 4 after "range motion." as a continuation of the paragraph.

In Column 5, Line 22, Change "26cm" to --26 cm--.

In Column 5, Line 42, Change "80and" to --80 and--.

In Columns 6-7, Lines 66-67 (Col. 6) and 1-3 (Col. 7), Delete "Connectors (78), attached to the brackets (42) of the knee member (12), provide the required connections. A similar connector (78) is provided on the motor (70). A two-part wire clamp (39A, 39B) on parts (254) allows to hold the wire on the support (38)." and insert the same on Line 65, Col. 6 after "thereof." as a continuation of the paragraph.

In Column 7, Line 64, Change "E2-512-250-i" to --E2-512-250-I--.

In Column 8, Line 3, Change "1 K" to --1K--.

Signed and Sealed this

Thirtieth Day of November, 2010

David J. Kappos  
*Director of the United States Patent and Trademark Office*

In Column 11, Line 48, Change "br" to --$b_r$--.

In Column 11, Line 65, Change "$\theta_{fix}=\pi-\pi-\theta_K-\beta$" to --$\theta_{fix}=\pi-\alpha-\theta_K-\beta$--.